United States Patent [19]
Haces et al.

[11] Patent Number: 6,110,916
[45] Date of Patent: Aug. 29, 2000

[54] HIGHLY PACKED POLYCATIONIC AMMONIUM, SULFONIUM AND PHOSPHONIUM LIPIDS

[75] Inventors: Alberto Haces; Valentina C. Ciccarone, both of Gaithersburg, Md.

[73] Assignee: Life Technologies, Inc., Rockville, Md.

[21] Appl. No.: 09/187,676

[22] Filed: Nov. 6, 1998

Related U.S. Application Data

[62] Division of application No. 08/782,783, Jan. 13, 1997, Pat. No. 5,834,439, which is a division of application No. 08/171,232, Dec. 20, 1993, Pat. No. 5,674,908.

[51] Int. Cl.[7] ............... A61K 31/495; C07D 241/04
[52] U.S. Cl. ............... 514/252.11; 424/1.21; 424/450; 435/829; 514/2; 514/19; 514/77; 514/170; 514/171; 514/252.12; 544/336; 544/357; 544/358
[58] Field of Search ............... 544/357, 336, 544/358; 514/252, 252.11, 252.12, 2, 19, 77, 170, 171; 424/450, 1.21; 435/829

[56] References Cited

U.S. PATENT DOCUMENTS

| | | | |
|---|---|---|---|
| 2,654,785 | 10/1953 | Miescher et al. | 564/295 |
| 2,867,665 | 1/1959 | Dornfeld | 260/606.5 |
| 3,324,182 | 6/1967 | DeBrunner et al. | 564/512 |
| 3,369,905 | 2/1968 | Jones et al. | 96/107 |
| 4,897,355 | 1/1990 | Eppstein et al. | 435/240.2 |
| 4,946,787 | 8/1990 | Eppstein et al. | 435/240.2 |
| 5,049,386 | 9/1991 | Eppstein et al. | 424/427 |
| 5,091,576 | 2/1992 | Bergeron | 564/367 |
| 5,171,678 | 12/1992 | Behr et al. | 435/172.3 |
| 5,208,036 | 5/1993 | Eppstein et al. | 424/450 |
| 5,264,618 | 11/1993 | Felgner et al. | 560/224 |
| 5,334,761 | 8/1994 | Gebeyehu et al. | 564/197 |
| 5,635,487 | 6/1997 | Wolff et al. | 514/44 |
| 5,674,908 | 10/1997 | Haces et al. | 514/642 |
| 5,736,392 | 4/1998 | Hawley-Nelson et al. | 435/320.1 |
| 5,744,335 | 4/1998 | Wolff et al. | 435/172.3 |
| 5,834,439 | 11/1998 | Haces et al. | 514/42 |
| 5,861,397 | 1/1999 | Wheeler | 514/247 |

FOREIGN PATENT DOCUMENTS

| | | |
|---|---|---|
| 158967 | 7/1952 | Australia. |
| 187 702 | 7/1986 | European Pat. Off.. |
| 394 111 A1 | 10/1990 | European Pat. Off.. |
| 290877 A1 | 6/1991 | German Dem. Rep.. |
| 892 413 | 3/1962 | United Kingdom. |
| WO91/04668 | 4/1991 | WIPO. |
| WO91/08191 | 6/1991 | WIPO. |
| WO91/15501 | 10/1991 | WIPO. |
| WO91/16024 | 10/1991 | WIPO. |
| WO93/19768 | 10/1993 | WIPO. |
| WO94/05624 | 3/1994 | WIPO. |
| 98/14439 | 4/1998 | WIPO. |
| 98/19709 | 5/1998 | WIPO. |

OTHER PUBLICATIONS

Budker, V. et al. (1997), "Protein/Amphipathic Polyamine Complexes Enable Highly Efficient Transfection with Minimal Toxicity," BioTechniques 23(1):139–147.

Barthel, F. et al. (1993), "Gene Transfer Optimization with Lipospermine–Coated DNA," DNA and Cell Biology 12(6):553–560.

Loeffler, J–P et al. (1993), "Gene Transfer into Primary and Established Mammalian Cell Lines with Lipopolyamine–Coated DNA," Meth. Enzymol. 217:599–618.

Zhou, X. et al. (1991), "Lipophilic polylysines mediate efficient DNA transfection in mammalian cells," Biochim. Biophys. Acta 1065:8–14.

Düzgünes, N. et al. (1989), "Fusion of Liposomes Containing a Novel Cationic Lipid, N–[2–3–(Dioleyloxy)propyl]–N,N,N–trimethylammonium: Induction by Multivalent Anions and Asymmetric Fusion with Acidic Phospholipid Vesicles," Biochem. 28:9179–9184.

Behr, J–P et al. (1989), "Efficient gene transfer into mammalian primary endocrine cells with lipopolyamine–coated DNA," Proc. Natl. Acad. Sci. USA 86:6982–6986.

Felgner, P.L. et al. (1987), "Lipofection: A highly efficient, lipid–mediated DNA–transfection procedure," Proc. Natl. Acad. Sci. USA 84:7413–7417.

Weinstock, L.T. et al. (1981), "Synthesis of New Polyamine Derivatives for Cancer Chemotherapeutic Studies," J. Pharm. Sci. 70(8):956–959.

Hetschko, M. and Gosselck, J. (1972), "Reaktionen von Sulfoniumsalzen DES 1,3–Dithiolans und Seiner 2,2–Substitutionsprodukte," Tetrahedron Lett. 17:1691–1692.

Primary Examiner—Richard L. Raymond
Attorney, Agent, or Firm—Greenlee, Winner and Sullivan, P.C.

[57] ABSTRACT

The present invention discloses highly packed polycationic ammonium, sulfonium and phosphonium lipid compounds useful for making lipid aggregates for delivery of macromolecules and other compounds into cells. They are especially useful for the DNA-dependent transformation of cells. Methods for their preparation and use as intracellular delivery agents are also disclosed.

57 Claims, No Drawings

HIGHLY PACKED POLYCATIONIC AMMONIUM, SULFONIUM AND PHOSPHONIUM LIPIDS

CROSS-REFERENCE TO RELATED APPLICATIONS

This application is a division of U.S. patent application Ser. No. 08/782,783, filed Jan. 13, 1997 now U.S. Pat. No. 5,834,439 which, in turn, is a division of U.S. patent application Ser. No. 08/171,232, filed Dec. 20, 1993, now U.S. Pat. No. 5,674,908, both of which are incorporated by reference herein to the extent not inconsistent herewith.

FIELD OF THE INVENTION

Highly packed polycationic ammonium, sulfonium and phosphonium lipid compounds are disclosed, having utility in lipid aggregates for delivery of macromolecules and other compounds into cells.

BACKGROUND OF THE INVENTION

Lipid aggregates such as liposomes have been found to be useful as agents for delivery to introduce macromolecules, such as DNA, RNA, protein, and small chemical compounds such as pharmaceuticals, to cells. In particular, lipid aggregates comprising cationic lipid components have been shown to be especially effective for delivering anionic molecules to cells. In part, the effectiveness of cationic lipids is thought to result from enhanced affinity for cells, many of which bear a net negative charge. Also in part, the net positive charge on lipid aggregates comprising a cationic lipid enables the aggregate to bind polyanions, such as nucleic acids. Lipid aggregates containing DNA are known to be effective agents for efficient transfection of target cells. aggregates containing DNA are known to be effective agents for efficient transfection of target cells.

The structure of various types of lipid aggregates varies, depending on composition and method of forming the aggregate. Such aggregates include liposomes, unilamellar vesicles, multilamellar vesicles, micelles and the like, having particle sizes in the nanometer to micrometer range. Methods of making lipid aggregates are by now well-known in the art. The main drawback to use of conventional phospholipid-containing liposomes for delivery is that the material to be delivered must be encapsulated and the liposome composition has a net negative charge which is not attracted to the negatively charged cell surface. By combining cationic lipid compounds with a phospholipid, positively charged vesicles and other types of lipid aggregates can bind DNA, which is negatively charged, can be taken up by target cells, and can transfect target cells. (Felgner, P. L. et al. (1987) Proc. Natl. Acad. Sci. U.S.A. 84:7413–7417; Eppstein, D. et al., U.S. Pat. No. 4,897,355.)

A well-known cationic lipid disclosed in the prior art is N-[1-(2,3-dioleoyloxy)propyl]-N,N,N-trimethylammonium chloride (DOTMA). The structure of DOTMA is:

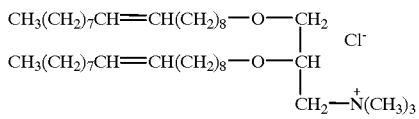

DOTMA by itself or in 1:1 combination with dioleoylphosphatidylethanolamine (DOPE) is formulated into liposomes using standard techniques. Felgner, et al. supra demonstrated that such liposomes provided efficient delivery of nucleic acids to some types of cells. A DOTMA:DOPE (1:1) formulation is sold under the trade name LIPOFECTIN (Gibco/BRL:Life Technologies, Inc., Gaithersburg, Md.). Another commercially available cationic lipid is 1,2-bis(oleoyloxy)-3-3-(trimethylammonia) propane (DOTAP), which differs from DOTMA only in that the oleoyl moieties are linked via ester, rather than ether bonds to the propylamine. DOTAP is believed to be more readily degraded by target cells. A related group of prior art compounds differ from DOTMA and DOTAP in that one of the methyl groups of the trimethyl-ammonium group is replaced by a hydroxyethyl group. Compounds of this type are similar to the Rosenthal Inhibitor (RI) of phospholipase A (Rosenthal, A. F. and Geyer, R. P. (1960) J. Biol. Chem. 235:2202–2206) which has stearoyl esters linked to the propylamine core. The dioleoyl analogs of RI are commonly abbreviated as DORI-ether and DORI-ester, depending on the linkage of the fatty acid moieties to the propylamine core. The hydroxy group can be used as a site for further functionalization, for example by esterification to carboxyspermine.

Another class of prior art compounds has been disclosed by Behr et al. (1989) Proc. Natl. Acad. Sci. U.S.A. 86:6982–6986; EPO publication 0 394 111 (Oct. 24, 1990), in which carboxyspermine has been conjugated to two types of lipids. The structure of 5-carboxyspermylglycine dioctadecylamide (DOGS) is:

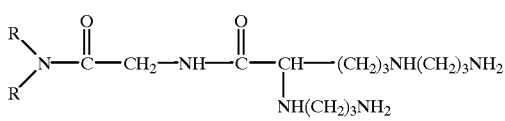

where $R=CH_3(CH_2)_{17}$

The structure of dipalmitoylphosphatidylethanolamine 5-carboxyspermylamide (DPPES) is:

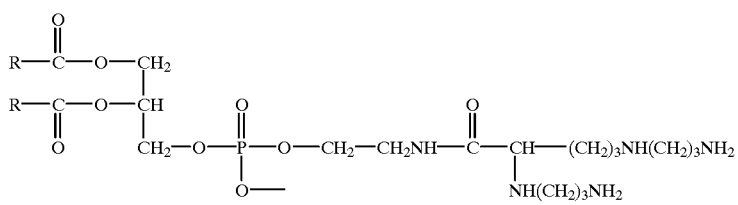

where $R=CH_3(CH_2)_{15}$

Both DOGS and DPPES have been used to coat plasmids, forming a lipid aggregate complex that provides efficient transfection. The compounds are claimed to be more efficient and less toxic than DOTMA for transfection of some cell lines. DOGS is available commercially as TRANSFECTAM™ (Promega, Madison, Wis.).

A cationic cholesterol derivative (DC-Chol) has been synthesized and formulated into liposomes in combination with DOPE. (Gao, X. and Huang, L. (1991) Biochim. Biophys. Res. Comm. 179:280–285) The compound's structure is

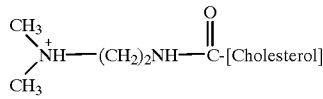

Liposomes formulated with DC-Chol are said to provide more efficient transfection and lower toxicity than DOTMA-containing liposomes for some cell lines.

Lipopolylysine, formed by conjugating polylysine to DOPE, has been reported to be especially effective for transfection in the presence of serum, a condition likely to be encountered in vivo (Zhou, X. et al. (1991) Biochim. Biophys. Acta 1065:8–14).

Despite advances in the field, a need remains for a variety of improved cationic lipid compounds. In particular, no single cationic lipid to date has been found to work well with all cell types. Since different cell types differ from one another in membrane composition, it is not surprising that different compositions and types of lipid aggregates are effective for different cell types, either for their ability to contact and fuse with target cell membranes, or for aspects of the transfer process itself. At present these processes are not well understood, consequently the design of effective liposomal precursors is largely empirical. Besides content and transfer, other factors are of importance, for example, ability to form lipid aggregates suited to the intended purpose, toxicity to the target cell, stability as a carrier for the compound to be delivered, and ability to function in an in vivo environment. In addition, lipid aggregates can be improved by broadening the range of substances which can be delivered to cells. The highly packed and spatially correct positioning of positive charges matching negative charges on DNA polycationic ammonium, sulfonium and phosphonium lipid compounds of the present invention have improved function with respect to several of the foregoing attributes.

SUMMARY OF THE INVENTION

The present invention provides highly packed polycationic ammonium, sulfonium and phosphonium lipid compounds according to the general formula:

Formula I

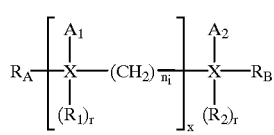

In the general formula (I),

X is selected from the group consisting of N, S, P or SO;

x is an integer ranging from 1 to about 20;

$n_i$, where i=1 to x, are, independently of one another, integers that can have a value ranging from 1 to about 6;

$R_A$ and $R_B$, independently of one another, are selected from the group consisting of H, or an alkyl, hydroxyalkyl or thiol substituted alkyl group having from 1 to about 6 carbon atoms;

$R_1$ and $R_2$, independently of one another, are selected from the group consisting of alkyl groups having from 1 to about 6 carbon atoms, where r is either 1 or 0, such that r is 0 or 1 when X is N, with N being positively charged if r is 1, r is 0 when X is S or SO, with S and SO being positively charged, and r is 1 when X is P, with P being positively charged; and $A_1$–$A_2$, independently of one another, are selected from the group consisting of the following groups $Z_1$–$Z_6$:

$Z_1$ is a straight-chain alkyl, alkenyl, or alkynyl group having from 2 to about 22 carbon atoms wherein one or more non-neighboring —$CH_2$— groups can be replaced with an O or S atom;

$Z_2$ is a branched alkyl, alkenyl, or alkynyl group having from 2 to about 22 carbon atoms wherein one or more non-neighboring —$CH_2$— groups can be replaced with an O or S atom;

$Z_3$ is a straight-chain or branched alkyl group substituted with one or two OH, SH, $NH_2$ or amine groups within about 3 carbon atoms of the bond between $Z_3$ and X;

$Z_4$ is a substituted straight-chain or branched alkyl, alkenyl or alkynyl group having from 2 to about 22 carbon atoms wherein the substituent is an aromatic, alicyclic, heterocyclic or polycyclic ring and wherein one or more of the non-neighboring —$CH_2$— groups of said alkyl, alkenyl or alkynyl group can be substituted with an O or S atom.

$Z_5$ is a -B-L group wherein B is selected from the group —CO—, —$CO_2$—, —OCO—, —CO—N—, —O—CO—N—, —O—$CH_2$—, —$CH_2$—O—, —S—$CH_2$—, —$CH_2$—S— or —$CH_2$— and L is selected from the group consisting of:

$Z_1$; $Z_2$; $Z_4$; or an aromatic, alicyclic, heterocyclic or polycyclic ring moiety;

$Z_6$ is a —CH(D-L)$_2$ or a —C(D-L)$_3$ group wherein D is selected from the group consisting of —CO—, —$CO_2$—, —OCO—,—CO—N—, —O—CO—N—, —O—, or —S— and L is selected from the group consisting of:

$Z_1$; $Z_2$; $Z_4$; or an aromatic, alicyclic, heterocyclic or polycyclic ring moiety.

In general in any particular compound of formula I, the chain length $n_i$ can vary from 1 to 6. For example, in a compound in which x is 3 where i is 1 to 3, $n_1$, $n_2$ and $n_3$ can all have the same value, any two can have the same value or all three can have different values. In particular embodiments of the compounds of this invention, the chain lengths $n_i$ vary in the repeating pattern 3, 4, 3, 3, 4, 3, . . . . Other particular embodiments of this invention include those in which $n_i$ differ from each other by +/−1.

A groups include those in which two substituents on different X's, preferably neighboring X groups, are covalently linked with each other to form a cyclic moiety.

The oxygen or sulfur atoms introduced into $Z_1$ and $Z_2$ groups are preferably introduced within about 3 carbon atoms from the bond to the X group.

The aromatic, alicyclic, heterocyclic or polycyclic ring moieties of this invention can be substituted or unsubstituted. Substituents include among others: OH, SH, $NH_2$, $CH_3$, $COCH_3$ and halogens, particularly F. Further, one or more of the ring carbons in the alicyclic, heterocyclic or polycyclic ring moieties of this invention can be carbonyl groups C=O.

Introduction of OH, $NH_2$ or amine groups as substituents on A groups within about 3 carbons from the bond to X can facilitate solubility of the compounds of this invention in physiological media.

Compounds of the invention are useful, either alone or in combination with other lipid aggregate-forming components (e.g., DOPE, DOSPA, DOTMA or cholesterol) for formulation into liposomes or other lipid aggregates. Such aggregates are polycationic, able to form stable complexes with anionic macromolecules, such as nucleic acids. The polyanion-lipid complex interacts with cells making the polyanionic macromolecule available for absorption and uptake by the cell.

Of special interest are the products of general formula (I) in which X is nitrogen and $A_1$ and $A_2$ are $Z_1$. These N-alkylated-polyamines and their quaternary ammonium salts are particularly useful for intracellular delivery of negatively charged macromolecules. This aspect of the invention is based on the finding that polyamines alkylated with long hydrocarbon chains have enhanced affinity for cells, many of which bear a net negative charge, and for various polyanions, such as nucleic acids, relative to the natural polyamine compounds. The effectiveness of N-alkylated polyamines is thought to result from the increased basicity (easier and stronger protonation) of the secondary and tertiary amines, even under alkaline conditions. Similarly, quaternized polyamine compounds show increased affinity for negatively charged substances, such as cells and nucleic acids, relative to the natural polyamines. The increase in affinity of the quarternized polyamine compounds presumably results from the permanent positive charges of the quarternized amines, each aligned in front of a negative charge of the DNA molecule (cooperative effect). Moreover, because of the relatively high lipid content of the alkylated and quaternized polyamines, these compounds also interact more strongly with the lipid bilayer of cell membranes than their cognate polyamines.

The combination of high lipid content per molecule and increased affinity for anionic macromolecules makes the compounds of the invention not only superior intracellular delivery agents, but also less toxic to the target cells. The reduced toxicity is thought to result in part from the fact that a higher binding constant between DNA/lipid leads to a lower concentration of lipid needed to completely coat the DNA. Since too much lipid disrupts the cell membrane (these lipids are also detergents), a lower amount of lipid should be less toxic. This increased affinity produces a more stable liposome, which in turn increases the efficiency of delivery. Thus, lower concentrations of these highly packed polycationic lipids are required to coat the molecules and bind to the target cells, thereby maximizing efficiency of delivery while minimizing cell toxicity.

In addition to the high lipid content and increased affinity for anionic substances, the compounds of the present invention also promote proximity between the complexed polyanion and the target cell membrane, thus increasing interactions between these two entities. In most liposomal precursors, the lipid moiety is physically separated from the cationic binding site by a relatively large linking group, typically ranging from five to eight carbon atoms in length. The present invention, in contrast, provides straight-chain compounds wherein the lipid constituent is directly attached, without a linker, to the cationic site. The branched compounds of the invention comprise a short (preferably 3 carbon) linker, which enhances the solubility of these highly packed lipids. It is believed that the unexpected improvement in efficiency and cell viability observed with these compounds can be attributed, at least in part, to proximity between the liposomal contents and cell membrane. Although the mechanism is not fully understood, it is believed that less water can intercalate in this region, thus minimizing disruption to the cell membrane caused by excess water.

Of particular interest are the products of general formula (I) in which X is nitrogen, n is 3 or 4, x is 1, r is 0, $R_A$ and $R_B$ are hydrogens, and $A_1$ and $A_2$ are unbranched alkyl, alkenyl, alkynyl or alkoxy groups having 2 to about 22 carbon atoms.

Most preferred is tetramethyltetrapalmylspermine, the product of general formula (I) in which X is nitrogen, where x is 3, $n_1$ is 3, $n_2$ is 4, and $n_3$ is 3, $R_A$ and $R_B$ are hydrogens, $R_1$ and $R_2$ are methyl groups, and $A_1$ and $A_2$ are unbranched alkyls having 16 carbon atoms.

Specific embodiments of this invention include compounds of formula I in which X is N. Of those compounds in which X is N, this invention includes, but is not limited to those compounds wherein:

$A_1$ and $A_2$, independently of one another, are selected from the group $Z_1$, $Z_2$, or $Z_3$;

$A_1$ and $A_2$, independently of one another, are selected from the group $Z_5$; and particularly those $Z_5$ wherein B is CO, —$CH_2$—, or —O—$CH_2$— and L is $Z_1$ or $Z_2$;

$A_1$ and $A_2$, independently of one another, are selected from the group $Z_6$; and particularly wherein D is —O—, —CO—, —OCO— or —$CO_2$—;

$R_A$ and $R_B$ are H or they are alkyl groups having 1–3 carbon atoms, inclusive;

$R_1$ and $R_2$ are alkyl groups having 1 to 3 carbon atoms, inclusive, and more particularly are methyl groups;

$n_i$ are all either 3 or 4 and x is 2 to 5;

$n_i$ alternate in the pattern 3, 4, 3, 3, 4, 3 and x is greater than or equal to 3; and $R_A$ and $R_B$ are —$CH_2$—$CH_2$—OH groups.

Compounds of this invention of formula I in which X is S include among others those in which:

$A_1$ and $A_2$ are R groups which are selected from any of $R_5$–$R_8$ where:
  R5 is a straight-chain (unbranched) alkyl, alkenyl, alkynyl or alkoxy having 2 to about 22 carbon atoms;
  R6 is a branched alkyl, alkenyl, alkynyl or alkoxy having 2 to about 22 carbon atoms;
  R7 is an aromatic, alicyclic, heterocyclic or polycyclic ring moiety; and
  R8 is a branched or unbranched substituted alkyl, alkenyl, alkynyl or alkoxy having from 2 to about 22 carbon atoms, wherein the substituent is an aromatic, alicyclic, heterocyclic or polycyclic ring.

Also included in this invention are compounds of formula I where X is S and x is 1. In this case, $R_A$ and $R_B$ are preferably methyl groups. Preferred A groups having alkyl, alkenyl alkynyl or alkoxy groups are those having about 12 to 16 carbon atoms. Preferred R are branched or straight-chain alkyl, alkenyl or alkynyl groups. In $R_5$, $R_6$, and the branched or straight-chain portion of $R_8$, one or more non-neighboring —$CH_2$— groups can be replaced with O or S atoms to give ether or thioether R groups.

Additional subsets of compounds of formula I of this invention include those in which:

x=1, n is an integer between 2 and 6 inclusive and R is an unbranched alkyl, alkenyl, alkynyl or alkoxy group having 2 to about 22 carbon atoms; and particularly those in which n is 3;

Wherein at least two of the R groups on different S are covalently linked together to produce a cyclic moiety.

In specific embodiments, the compounds of the present invention are also represented by the formulas II and III:

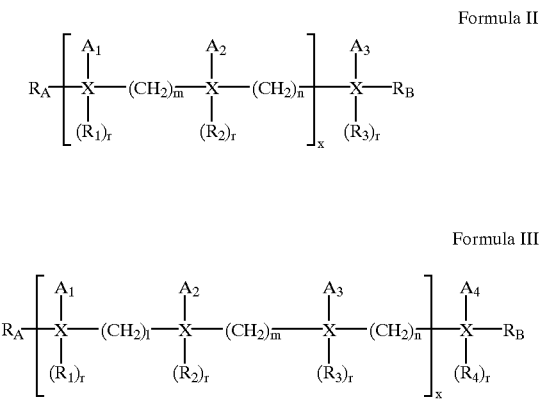

In both formula II and III, $R_A$, $R_B$, r, $Z_1$–$Z_6$ and X are as defined above for formula I. All of $R_1$–$R_4$ can be selected from the groups as defined above for $R_1$ and $R_2$.

In formula II:
n and m, independently of one another, are integers (chain length) ranging in value from 1 to about 6, with n and m of 3 or 4 being more preferred. It is preferred that the values of m and n differ only by +/−1;

x can be an integer from 1 to 10, with the subset of compounds having x=2–5 being of particular interest; and $A_1$–$A_3$, independently of one another, are selected from the group $Z_1$–$Z_6$, of particular interest are A groups which are straight-chain alkyl, alkenyl or alkynyl groups.

In formula III:
l, m, and n, independently of one another, are integers (chain length) ranging in value from 1 to about 6, with l, m and n of 3 or 4 being more preferred. It is preferred that the values of l, m and n differ from each other only by +/−1;

x can be an integer from 1 to 10, with the subsets of compounds having x=1, x=2 and x=3–5 being of particular interest; and $A_1$–$A_4$, independently of one another, are selected from the group $Z_1$–$Z_6$, with A groups which are straight-chain alkyl, alkenyl or alkynyl groups of particular interest.

Specific embodiments of this invention include compounds of formulas II and III in which X is N, m is 3, and n is 4, wherein $A_1$–$A_3$, independently of one another, are selected from the groups $Z_1$, $Z_2$, and $Z_3$, and wherein $A_1$–$A_3$ are the same group. Other specific embodiments include compounds of formulas II and II in which X is N and $A_1$–$A_3$, independently of one another, are selected from the group $Z_5$, wherein B is CO, —$CH_2$—, or —O—$CH_2$— and L is $Z_1$ or $Z_2$. Other embodiments include compounds of formulas II and III in which X is N and $A_1$–$A_4$, independently of one another, are selected from the group $Z_6$, wherein D is —O—, —CO—, —OCO— or —$CO_2$—. Of particular interest are compounds of formulas II and III wherein X is N and $R_A$ and $R_B$ are H or methyl groups, $R_1$ and $R_2$ are methyl groups, m is 3, n is 4, x is 2 to 6. Also of particular interest are compounds of formulas II and III wherein X is N and $R_A$ and $R_B$ are —$CH_2$—$CH_2$—OH groups.

Of particular interest are compounds of formula III in which X is N; $R_A$ and $R_B$ are H; l, m and n are 3 or 4; x is 1; and $A_1$–$A_4$, independently of one another, are unbranched alkyl groups having from about 12 to 16 carbon atoms. Particularly preferred are compounds of formula III where $A_1$–$A_4$ are all the same unbranched alkyl group, particularly an unbranched alkyl group having 16 carbon atoms. Other embodiments include compounds of formula III wherein X is N; x is 1; l, m and n are 3 or 4; and $A_1$–$A_4$ is $Z_5$, wherein B is CO and L is $Z_1$, particularly wherein $Z_1$ has about 12 to about 16 carbon atoms. Other specific embodiments include the compounds of formula III wherein X is S; x is 1–5; l, m and n are 2 or 3; and $A_1$–$A_4$ is $Z_1$, particularly wherein $A_1$–$A_4$ are unbranched alkyl or alkenyl groups having from 2 to about 22 carbon atoms, and preferably from about 12 to about 16 carbon atoms. Also of interest are compounds of formula III wherein at least two of the $A_1$–$A_4$ are substituents are covalently linked to produce a cyclic compound. Other specific embodiments include the compounds of formula III wherein X is P.

In compounds of both formula II and III, preferred Z groups are branched or straight-chain alkyl, alkenyl, alkynyl or alkoxy groups, have about 12 to about 16 carbon atoms.

This invention also includes compounds having the structure:

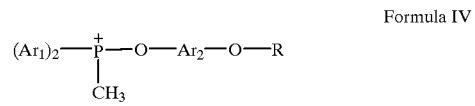

wherein $Ar_1$ and $Ar_2$ are aryl rings or cyclohexane rings and R is selected from any of $R_5$–$R_8$ as defined above. The aryl rings can be selected from among any of phenyl, pyridinyl, pyrimidyl, pyrazinyl, thiadiazole and pyridazinyl. Cyclohexane rings include trans-cyclohexyl rings. Of particular interest are compounds of formula IV wherein both of $Ar_1$ and $Ar_2$ are phenyl rings, and wherein R is $R_5$ or an unbranched alkyl.

This invention also includes lipid aggregates comprising one or more of the compounds of formulas I, II, III or IV or mixtures thereof. Of particular interest are lipid aggregates of the compounds of formula I, more particularly those in which X is N.

The transfection methods of the present invention employing compounds of formulas I, II, III or IV or mixtures thereof can be applied to in vitro and in vivo transfection of cells, particularly to transfection of eukaryotic cells including animal cells. The methods of this invention can be used to generate transfected cells which express useful gene products. The methods of this invention can also be employed as a step in the production of transgenic animals. The methods of this invention are useful as a step in any therapeutic method requiring introducing of nucleic acids into cells. In particular, these methods are useful in cancer treatment, in in vivo and ex vivo gene therapy, and in diagnostic methods. The transfection compositions of this invention can be employed as research reagents in any transfection of cells done for research purposes. Nucleic acids that can be transfected by the methods of this invention include DNA and RNA from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (Ribozymes), and those which function in diagnostic assays.

The compositions and methods provided herein can also be readily adapted in view of the disclosure herein to introduce biologically active anionic macromolecules other than nucleic acids including, among others, polyamines, polyamine acids, polypeptides, proteins, biotin, and polysaccharides into cells. Other materials useful, for example as therapeutic agents, diagnostic materials and research reagents, can be complexed by the polycationic lipid aggregates and introduced into cells by the methods of this invention.

This invention also includes transfection kits which include one or more of the compounds of formulas I, II, III, IV or mixtures thereof as cationic lipids.

DETAILED DESCRIPTION OF THE INVENTION

The present invention provides novel, highly packed polycationic ammonium, sulfonium and phosphonium lipid compounds having unique properties and advantages not heretofore available to the liposome art. The compounds can be used alone or in combination with other compounds (e.g., DOPE, DOTMA and DOSPA) to prepare liposomes and other lipid aggregates suitable for transfection or delivery of compounds other than DNA to target cells, either in vitro or in vivo.

The novel compounds of general formula (I) are polycationic and thus form highly stable complexes with various anionic macromolecules, particularly polyanions such as nucleic acids. These compounds have the property, when dispersed in water, of forming lipid aggregates which associate strongly, via their cationic portions, with polyanions. By using an excess of cationic charges relative to the anionic compound, the polyanion-lipid complexes may be adsorbed on cell membranes, thereby facilitating uptake of the desired compound by the cells.

The cationic lipids disclosed herein offer three unique advantages over prior art compounds. First, the compounds of general formula (I) represent novel liposomal precursors wherein the polycationic binding regions are optimally spaced, preferably equidistance between charges, to provide proper alignment with the anionic phosphates of nucleic acids. Proper alignment of charges increases the binding constant of the lipid to nucleic acid via cooperative interaction. This increased affinity produces a more stable DNA-lipid complex, which in turn increases the efficiency of delivery. Thus, lower concentrations of these agents are required to coat the molecules and bind to the target cells, thereby maximizing efficiency of delivery while minimizing cell toxicity.

The second unique advantage of the compounds disclosed herein is their unusually high affinity for the lipid bilayer of cell membranes. Unlike the mono-substituted lipopolyamine compounds currently in use, the compounds of the invention comprise lipidic substituents at each cationic binding region. Compounds of the invention thus interact more strongly with the lipid bilayer of cell membranes than existing cationic lipids. The branched lipids of the present invention comprise multiple lipid moieties per cationic site, and thus bind particularly strongly to cell membranes.

Finally, the compounds of the present invention promote proximity between the complexed polyanion and the target cell membrane, thus increasing interactions between these two entities. Unlike previous cationic lipids, the lipid moieties of the present compounds are attached without linkers to the cationic sites.

Of special interest are the products of general formula (I) in which X is nitrogen and $A_1$ and $A_2$ are $Z_1$. These N-alkylated-polyamines and their quaternary ammonium salts are especially useful for intracellular delivery of negatively charged macromolecules. The unexpected effectiveness is thought to result from the increased basicity and the permanent positive charge of the alkylated and quarternized polyamines, respectively. Moreover, as discussed elsewhere herein, the relatively high lipid content of these compounds is believed to maximize interaction with the lipid bilayer of cell membranes. The combination of high lipid content and increased affinity for anionic macromolecules makes these compounds not only superior intracellular delivery agents, but also less toxic to the target cells.

In a preferred embodiment of general formula (I), the values of $n_i$ are either identical or vary at most by one integer, thus providing approximately equidistant spacing between the polycationic binding regions (X). In another preferred embodiment of general formula (I), when $A_1$ and $A_2$ are branched hydrocarbons (e.g., $Z_2$), each branch is connected to the polymer backbone via a hydrophilic heteroatom such as oxygen, as exemplified herein. The presence of a hydrophilic heteroatom mitigates the hydrophobicity of these highly packed compounds, thus enhancing their solubility in water.

Certain of the compounds of this invention may be insufficiently soluble in physiological media to employ for delivery and transfection methods. Those of ordinary skill in the art will appreciate that there are a variety of techniques available in the art to enhance solubility of such compounds in aqueous media. Such methods are readily applicable without undue experimentation to the compounds described herein. As described herein, one method for increasing solubility of compounds of Formulas I through III is to introduce OH, $NH_2$, SH, or amine substituents on Z groups within about 3 carbon atoms from the X group.

The present invention also provides improved methods for transfecting and delivering macromolecules to target cells. The improvement relates to the use of highly packed polycationic ammonium, sulfonium and phosphonium lipid compounds to either enhance the efficiency of delivery or to reduce the toxicity to the cells. This invention has significant advantages over prior art methods which employ neutral or slightly basic delivery agents having a relatively low lipid content, which interact weakly with both anionic macromolecules and the lipid bilayer of cell membranes. Because of this limited affinity and low lipid content, current methods require high concentrations of the delivery agent, which disrupts cell membranes, often leading to cell death. The present invention resolves the problems associated with prior art methods by employing highly efficient delivery agents which are effective at relatively low and non-toxic concentrations.

DEFINITIONS

Lipid Aggregate is a generic term which includes liposomes of all types both unilamellar and multilamellar as well as micelles and more amorphous aggregates of cationic lipid or lipid mixed with amphiphatic lipids such as phospholipids.

Target Cell refers to any cell to which a desired compound is delivered, using a lipid aggregate as carrier for the desired compound.

Transfection is used herein to mean the delivery of expressible nucleic acid to a target cell, such that the target cell is rendered capable of expressing said nucleic acid. It will be understood that the term "nucleic acid" includes both DNA and RNA without regard to molecular weight, and the term "expression" means any manifestation of the functional presence of the nucleic acid within the cell, including without limitation, both transient expression and stable expression.

Delivery is used to denote a process by which a desired compound is transferred to a target cell such that the desired compound is ultimately located inside the target cell or in, or on, the target cell membrane. In many uses of the compounds of the invention, the desired compound is not readily taken up by the target cell or appropriate cytoplasmic compartment and delivery via lipid aggregates is a means for getting the desired compound into the cell cytoplasm.

The polycationic lipids were prepared by following the general reaction schemes given below (Schemes 1–5).

Straight-chain polycationic lipopolyamines were prepared as shown in Scheme 1. A polyamine was treated with an acid chloride of the desired length in the presence of triethylamine and methylene chloride under argon at room temperature to obtain the corresponding substituted amide (compound 1). Compound 1 was then reduced using lithium aluminum hydride in the presence of anhydrous tetrahydrofurane to give compound 2. Treatment of compound 2 with iodomethane at high temperature yielded a partially quarternized compound (compound 3). Compound 3 was further methylated using additional iodomethane to produce the fully quarternized spermine derivative (compound 4).

Although the above method exemplifies the synthesis of N,N,N',N'-tetrapalmylspermine and its quarternized derivatives, the reaction scheme provides a general method for preparing a variety of N-alkylated and quarternized lipopolyamines. Those of ordinary skill in the art will appreciate that alternate methods and reagents other those specifically detailed herein can be employed or readily adapted to produce a variety of useful compounds. For example, although the above reaction scheme uses spermine as the exemplified starting material, the scheme is equally applicable with other straight-chain polyamines. Various polyamines are readily accessible or can be easily synthesized using standard methods, for example, by combining acrylonitrile with an appropriate diaminoalkane.

Branched polycationic lipopolyamines are prepared as shown in Scheme 2. A branched amino alcohol is treated with an appropriate nitrile (e.g., acrylonitrile) to produce a branched amino nitrile of the desired length (compound 4). Compound 4 is then alkylated using 3-bromo-acrylonitrile at high temperature to yield the corresponding dinitrile compound (compound 5). Compound 5 is further alkylated using an alkyl sulfonate in pyrrole to yield compound 6. Reduction of the nitrilo groups of compound 6 using lithium aluminum hydride or, alternatively, using hydrogen in the presence of Raney nickel, yields compound 7. Compound 7 is then treated with an acid chloride of the desired length in the presence of triethylamine and methylene chloride, followed by reduction with lithium aluminum hydride at high temperature to give compound 8.

Although the above method uses tri-hydroxymethyl-aminomethane as the exemplified starting material, the reaction scheme provides a general method for preparing a variety of branched lipopolyamines. These alkylated polyamines can also be quarternized as previously described (see compounds 3 and 4 above) using iodomethane at high temperature. Those of ordinary skill in the art will appreciate that alternate methods and reagents can be employed or readily adapted to produce a variety of useful branched compounds.

Dicationic sulfonium lipids were prepared as shown in Scheme 3. 1,3-propanedithiol was treated with ethylene oxide to afford the corresponding diol-adduct. The diol was tosilated in the presence of base followed by displacement of the tosyl groups by sodium sulfide to give the corresponding mercaptan. This mercaptan was di-alkylated with acetyl bromide using N-butyl lithium as the base. Finally, treating the tetra sulfide with iodomethane affords the sulfonium salt. Polycationic sulfonium lipids were prepared as shown in Scheme 4. Schemes 3 and 4 provide a general method for preparing a variety of highly packed sulfonium lipids. Modification and optimization of this method to produce a variety of useful sulfonium compounds is well within the skill of the ordinary artisan.

Phosphonium lipids were prepared as shown in Scheme 5. Diphenylphosphinic chloride was treated with hydroquinine (excess) to afford the corresponding addition product. Treatment of the addition product with sodium hydride followed by acetyl bromide afforded the corresponding phospholipid. The phospholipid, in turn, is quarternized with iodomethane to afford the phosphonium salt.

The compounds of the invention can be used in the same manner as are prior art compounds such as DOTMA, DOTAP, DOGS and the like. Methods for incorporating such cationic lipids into lipid aggregates are well-known in the art. Representative methods are disclosed by Felgner et al., supra; Eppstein et al. supra; Behr et al. supra; Bangham, A. et al. (1965) M. Mol. Biol. 23:238–252; Olson, F. et al. (1979) Biochim. Biophys. Acta 557:9–23; Szoka, F. et al. (1978) Proc. Natl. Acad. Sci. U.S.A. 75:4194–4198; Mayhew, E. et al. (1984) Biochim. Biophys. Acta 775:169–175; Kim, S. et al. (1983) Biochim. Biophys. Acta 728:339–348; and Fukunaga, M. et al. (1984) Endocrinol. 115:757–761. Commonly used techniques for preparing lipid aggregates of appropriate size for use as delivery vehicles include sonication and freeze-thaw plus extrusion. See, e.g., Mayer, L. et al. (1986) Biochim. Biophys. Acta 858:161–168. Microfluidization is used when consistently small (50–200 nm) and relatively uniform aggregates are desired (Mayhew, E., supra). Aggregates ranging from about 50 nm to about 200 nm diameter are preferred; however, both larger and smaller sized aggregates are functional.

Methods of transfection and delivery of other compounds are well-known in the art. The compounds of the present invention yield lipid aggregates that can be used in the same processes as those prior art compounds.

It will be readily apparent to those of ordinary skill in the art that a number of general parameters are important for optimal efficiency of transfection or delivery. These parameters include, for example, the polycationic lipid concentration, the concentration of compound to be delivered, the medium employed for delivery, the length of time the cells are incubated with the polyanion-lipid complex, and the relative amounts of cationic and non-cationic lipid. It may be necessary to optimize these parameters for each particular cell type. Such optimization is routine employing the guidance provided herein, including the transfection assays as described in the Examples herein.

It will also be apparent to those of ordinary skill in the art that alternative methods, reagents, procedures and techniques other than those specifically detailed herein can be employed or readily adapted to produce the liposomal precursors and transfection compositions of this invention. Such alternative methods, reagents, procedures and techniques are within the spirit and scope of this invention.

The preparation and use of representative compounds of the invention are further detailed by reference to the following Examples. In each case, the ability of various compounds of the invention to provide efficient transfection was compared with a control using DOSPA:DOPE (1.5:1 molar ratio). All abbreviations used herein are standard abbreviations in the art. Specific procedures not described in detail are either referenced or well-known in the art.

EXAMPLES

Example 1

Synthesis of N,N,N',N'-tetrapalmitoylspermine (1)

To a solution of spermine (0.99 g, 80%, 3.8 mmol) and triethylamine (1.54 g, 15.2 mmol) in methylene chloride (400 ml) at 0° C. under argon was added palmitoyl chloride (4.17 g, 4.8 ml, 15.2 mmol). The reaction continued at room temperature for three days. TLC analysis (silica gel; $THF:CH_2Cl_2/1:3$) showed a new spot (rf=0.8) and no starting material. The organic phase was washed twice with sodium bicarbonate solution (10%, 200 ml), hydrochloric acid (1 M, 200 ml) and water (200 ml). The solution was dried ($Na_2SO_4$) and the solvent removed to afford 4 g of desired product (90%).

Example 2

Synthesis of N,N,N'N'-tetrapalmylspermine (2)

To a suspension of lithium aluminum hydride (900 mg, 23.7 mmol) in anhydrous tetrahydrofurane (80 ml) was added a solution of N,N,N',N'-tetrapalmitoylspermine (500 mg, 0.43 mmol) in anhydrous tetrahydrofurane (10 ml). The reaction mixture was refluxed for two days under argon. The excess lithium aluminum hydride was removed with sodium hydroxide (1 M, 5 ml). The organic phase was decanted and the flask washed twice with additional tetrahydrofurane (50 ml). The solution was dried (Na2SO4) and the solvent removed in vacuo to afford almost pure desired tetraamine. This material was passed through a short-path silica gel bed (filtration) and eluted sequentially with ethyl acetate and ethyl acetate/triethylamine (10%) to afford, after solvent removal, the desired product (313 mg, 82%).

Example 3

Synthesis of N,N,N',N'-tetramethyltetrapalmyl-sperminetetrammonium iodide (3)

A solution of tetrapalmylspermine (20 mg) in iodomethane (1 ml) was heated at 55° C. for 18 hr. The excess iodomethane was removed in vacuo and the residue redissolved in methylene chloride. This solution was extracted twice with sodium bicarbonate (3 ml), dried (NaSO4), and the solvent removed to afford 25 mg (100%) of desired material.

Example 4

Synthesis of N,N,N',N'-hexamethyltetrapalmyl-sperminetetrammonium iodide (4)

A solution of N,N,N',N'-tetramethyltetrapalmylspermine-tetrammonium iodide (10 mg) in iodomethane was heated for 48 hr at 80° C. The iodomethane was removed in vacuo to afford 12 mg of desired product (100%).

Example 5

Lipid Formulation

Tetrapalmylspermine, tetramethylpalmyl-spermine, and hexamethylpalmylspermine were formulated using two protocols. Lipids were first dissolved in chloroform and aliquots of each lipid with and without DOPE were evaporated under vacuum. Lipids were then resuspended directly in water by vortexing, or were suspended first in ethanol (1/10 of final volume) and then diluted with water.

Example 6

Cell Culture and Plasmids

All cell lines were obtained from American Type Culture Collection (Rockville, Md.). Standard tissue culture methods were employed. Chinese hamster ovary (CHO-K1) cells were cultured in EMEM (GIBCO BRL) containing 2 mM proline and 5% (v/v) fetal bovine serum (FBS). NIH 3T3 cells were cultured in Dulbecco's-modified Eagle's medium (DMEM) containing 10% (v/v) calf serum (CS). Jurkat cells were cultured in RPMI 1640 (GIBCO BRL) containing 10% (v/v) FBS. Human fibroblasts were isolated from neonatal foreskin tissue and prepared as follows. Rinsed, fresh tissue was exposed to 25 units/ml dispase (Collaborative Research, Bedford, Mass.) overnight at 4° C., separated into epidermis and dermis, and the minced dermis was digested 10 min at 37° C. in 0.25% (v/v) trypsin, 1 mM EDTA. The reaction was stopped by a rinse and centrifugation in DMEM with 10% (v/v) FBS, in which the cells were also cultured. All cultures were incubated at 37° C., 5% $CO_2$. Media for all cultures routinely included 100 units/ml penicillin and 100 μg/ml streptomycin.

The plasmid vector pCMV β-gal is a commercially available (Clontech, Calif.) mammalian reporter vector containing the *E. coli* β-galactosidase (β-gal) gene under the control of the Cytomegalovirus promoter (see MacGregor et al. (1989) Nucleic Acids Res. 17:2365). The plasmid vector pCMVCAT was also described previously (Boshart et al. (1985) Cell 41:521). Plasmid DNA was purified by standard cesium chloride methods.

Example 7

Transfection of CHO-K1, NIH-3T3, and Human Fibroblast Cells

For transfection of CHO-K1, NIH-3T3, and human fibroblast cells in 24-well-plates, lipid and DNA (pCMV β-gal) were diluted separately into 25 μl aliquots of Opti-MEM I Reduced Serum Medium (GIBCO BRL; serum-free). These aliquots were gently mixed and incubated at room temperature for 15–45 minutes to form lipid-DNA complexes. The complexes were added to cells in each well containing 250 μl serum-free growth medium. Cells were exposed to DNA-lipid complexes for 4–5 hr under standard culture conditions, after which 1 ml normal growth medium was added. Antibiotics were never present during lipid-mediated transfections. At 24 hr after transfection, cells were assayed in situ for β-galactosidase activity.

Example 8

Transfection of Jurkat Cells

For transfection of Jurkat cells in suspension, lipid and DNA (pCMVCAT) were diluted separately into 500 μl aliquots of Opti-MEM I Reduced Serum Medium (GIBCO BRL; serum-free). These aliquots were gently mixed and incubated at room temperature for 15–45 minutes to form lipid-DNA complexes. For each transfection sample, 1×10⁶ Jurkat cells were centrifuged in a microfuge tube. The cell pellets were suspended with the lipid-DNA complex solutions and transferred to wells of 12-well plates. Cells were exposed to DNA-lipid complexes for 4–5 hr under standard culture conditions, after which 0.5 ml growth medium containing 30% FBS, 150 µg/ml Phorbol myrystate acetate (PMA; Sigma Chemical Co., St. Louis, Mo.), and 3 µg/ml phytohemagglutinin (PHA) were added to a final concentration of 10% FBS, 50 µg/ml PMA and 1 µg/ml PHA, respectively. After approximately 24 hr, one ml growth medium containing 10% FBS, 50 ng/ml PMA and 1 µg/ml PHA was added to each well. Antibiotics were never present during lipid-mediated transfections. Cells were harvested at approximately 48 hr post-transfection by centrifugation. Cell lysates were prepared by resuspending cell pellets at 0° C. in 1 M Tris-HCl pH 8.0 containing 0.1% Triton X-100 and 5 µl aliquots were assayed for CAT activity.

Example 9

Transient Transfection Assays

Cell lysates were assayed for β-galactosidase activity as described by Sanes et al. (1986) EMBO J. 5:3133. Cells were rinsed with PBS, fixed for 5 minutes in 2% (v/v) formaldehyde, 0.2% glutaraldehyde in PBS, rinsed twice with PBS, and stained 2 hr to overnight with 0.1% β-gal, 5 mM potassium ferrocyanide, 5 mM potassium ferrocyanide, 2 mM $MgCl_2$ in PBS. Rinsed cells were photographed using a 10× or 20× objective on a Nikon inverted microscope with Hoffman optics. Transfection efficiency is evaluated by counting or estimating the number of β-gal positive cells (blue-stained cells).

Cell lysates were assayed for CAT activity as described by Neumann et al. (1987) BioTechniques 5:444. Cells were rinsed with PBS and frozen at −70° C. in 0.5–1.5 ml 0.1% Triton X-100 in 0.1 M Tris, pH 8.0. After rapid thawing at 37° C., the lysate was cleared by centrifugation. When more than 5 µl of a 1 ml extract was to be used in the assay, the extract was heated to 65° C. for 10 minutes to inactivate any deacetylases present, and centrifuged again. When necessary, the extract was diluted in 0.1 M Tris pH 7.8–8.0. Lysate was incubated with 50nCi $^{14}C$ Butyryl CoA (New England Nuclear, Boston, Mass.) and 0.25 µMoles chloramphenicol in 0.1 M Tris, pH 7.8–8.0, in a total volume of 0.25 ml in a 4-ml scintillation vial. Reaction mixtures were incubated at 37° C. for 2 hr, overlaid with 3 ml Econofluor (Dupont, Boston, Mass.), inverted once and then incubated for an additional 2 hr at room temperature before counting. Each assay included a standard curve of 0.001 to 0.05 units CAT enzyme (Pharmacia, Uppsala, Sweden), the linear range for these reaction conditions. Extracts were diluted or volumes were adjusted in order to have activity within the linear range during the assay. To insure accuracy, the activity was normalized to the same volume per transfection.

Example 10

Results

Results are shown in Tables 1–4. The "CAT ACTIVITY" column in Table 4 indicates the relative transfection effectiveness of the lipid formulation in Jurkat cells. The control sample was a cell culture grown under similar conditions as those that were transfected, but with no DNA or cationic lipid added.

For primary human fibroblast cells (Table 1), NIH-3T3 cells (Table 2), CHO-K1 cells (Table 3), and Jurkat cells (Table 4), compound 3 was highly effective for DNA transfection with minimal toxicity. Data in Tables 1–4 show that compound 3 has efficiency comparable to DOSPA for the transfection of human fibroblasts and Jurkat cells, but a lower concentration of lipid is required for optimal activity. When using low amounts of DNA in NIH-3T3 cells, compound 3 was approximately 10-fold more effective than DOSPA.

TABLE 1

TRANSFECTION RESULTS WITH PRIMARY HUMAN FIBROBLASTS

| Lipid (Molar ratio) | Optimal Lipid Conc. (µg) | β-gal Positive Cells (app. %) |
|---|---|---|
| Compound 3:DOPE (1:1) | 1 | 5 |
| DOSPA:DOPE (1.5:1) | 5 | 5 |

Cells were plated in 24-well plates at a density of $3 \times 10^4$ cells per well. The following day, cells in each well were transfected with a suboptimal concentration (200 ng) of pCMV β-gal DNA, using the indicated lipid formulations.

TABLE 2

TRANSFECTION RESULTS WITH NIH-3T3

| Lipid (Molar ratio) | Optimal Lipid Conc. (µg) | β-gal Positive Cells (app. %) |
|---|---|---|
| Compound 3:DOPE (1:1) | 1 | 10 |
| DOSPA:DOPE (1.5:1) | 4 | 1 |

Cells were plated in 24-well plates at a density of $4 \times 10^4$ cells per well. The following day, cells in each well were transfected with a suboptimal concentration (200 ng) of pCMV β-gal DNA, using the indicated lipid formulations.

TABLE 3

TRANSFECTION RESULTS WITH CHO-K1

| Lipid (Molar ratio) | Optimal Lipid Conc. (µg) | β-gal Positive Cells (app. %) |
|---|---|---|
| Compound 3:DOPE (1:1) | 1–1.2 | 20 |
| DOTMA:DOPE (1:1) | 1.5 | 10–15 |
| DOSPA:DOPE (1.5:1) | 3–5 | 80–90 |

Cells were plated in 24-well plates at a density of $6 \times 10^4$ cells per well. The following day, cells in each well were transfected with 200 ng of pCMV β-gal DNA, using the indicated lipid formulations.

TABLE 4

TRANSFECTION RESULTS WITH JURKAT CELLS

| Lipid (Molar ratio) | Optimal Lipid Conc. (µg) | CAT Activity (mUnits CAT/5 µl) |
|---|---|---|
| Compound 3:DOPE | 6 | 19.8 |
| DOTMA:DOPE (1:1) | 5 | 5.0 |
| DOSPA:DOPE (1.5:1) | 25 | 19.2 |

Cells ($1 \times 10^6$) were transfected with 2 µg of pCMVCAT DNA as described above, using the indicated lipid formulations. At 48 hr post-transfection, cell lysates were prepared and 5 µl aliquots were assayed for CAT enzyme activity.

SCHEME 1
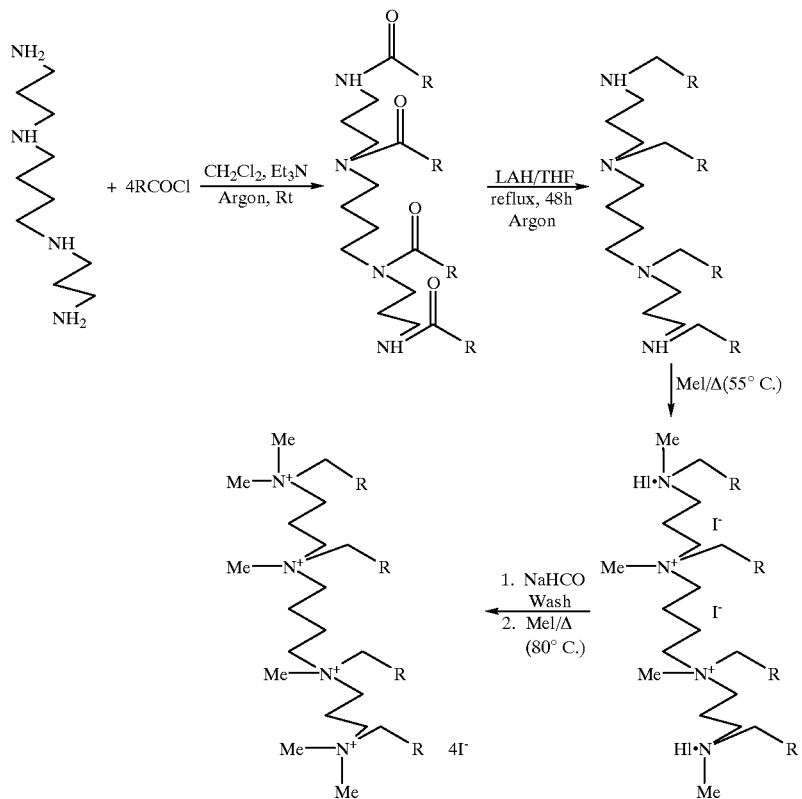
SCHEME 2
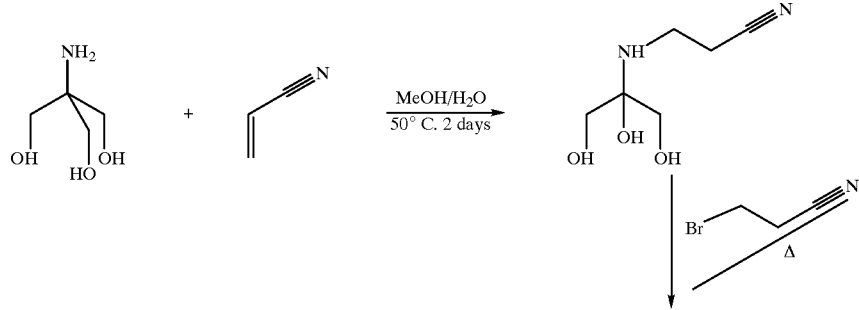

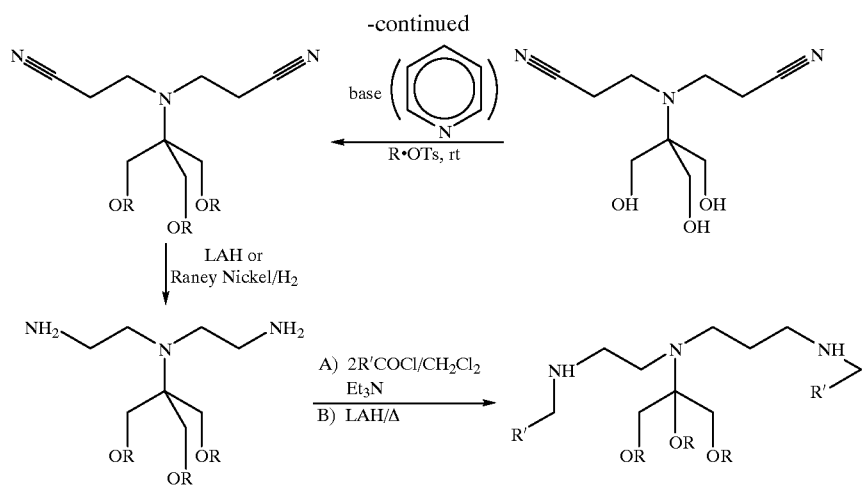
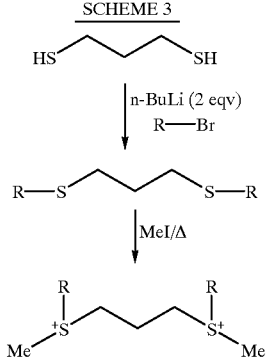
SCHEME 3
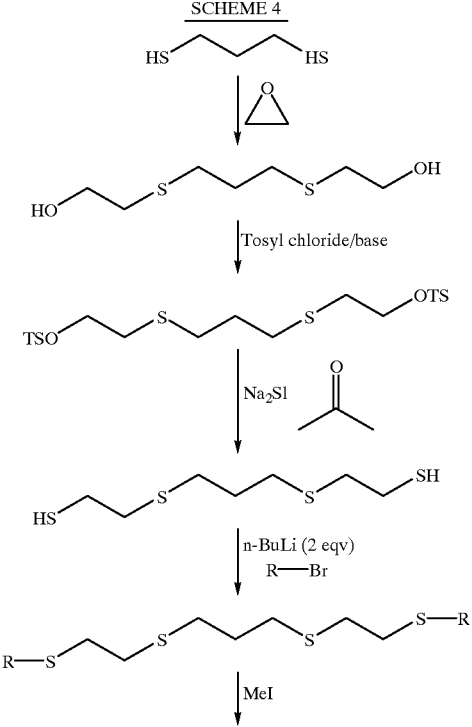
SCHEME 4
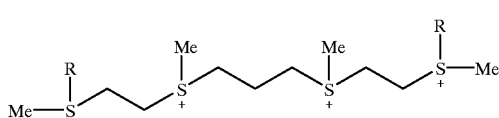
SCHEME 5
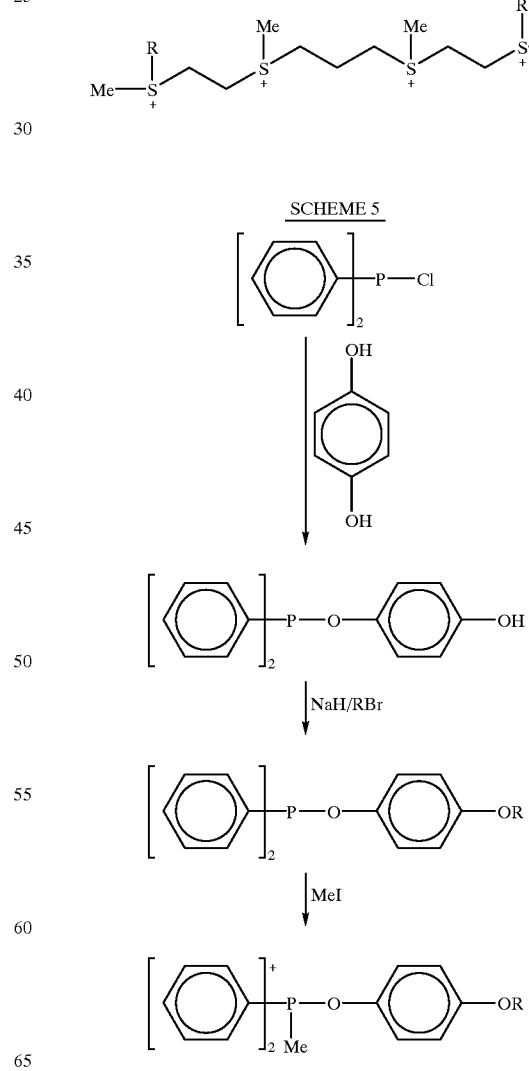

We claim:

1. A compound having the formula:

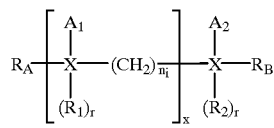

and salts thereof where:

X is N;

x is an integer ranging from 1 to about 20;

$n_i$, where i–1 to x, independently of one another, are integers that can have a value ranging from 1 to about 6;

r is 0 or 1 with N positively charged when r is 1;

$R_A$ and $R_B$, independently or one another, are selected from the group consisting of H, an alkyl, hydroxyalkyl and thiol-substituted alkyl group having from 1 to 6 carbon atoms except that when x=1, $R_A$ and $R_B$ are not hydrogens;

$R_1$ and $R_2$, independently of other $R_1$ and $R_2$, are selected from the group consisting of alkyl groups having from 1 to about 6 carbon atoms;

$A_1$, independently of other $A_1$ groups, and $A_2$ are selected from the group consisting of the groups:
(a) a straight-chain or branched alkyl, alkenyl, or alkynyl group having from 2 to about 22 carbon atoms wherein one or more non-neighboring —$CH_2$— groups can be replaced with an O or S atom;
(b) a straight-chain or branched alkyl group substituted with one or two OH, SH, $NH_2$ or amine groups within about 3 carbon atoms of the bond between $A_1$ or $A_2$ and N;
(c) a substituted straight-chain or branched alkyl, alkenyl or alkynyl group having from 2 to about 22 carbon atoms wherein the substituent is an aromatic, alicyclic heterocyclic or polycyclic ring and wherein one or more of the non-neighboring —$CH_2$— groups of said alkyl, alkenyl or alkynyl group can be substituted with an O or S atom;
(d) a-B-L group where B is selected from the group consisting of —CO—, —$CO_2$—, —O—C—O—, —CO—NH—, —O—CO—NH—, —O—$CH_2$—, —S—$CH_2$—, —$CH_2$—S—, and —$CH_2$— and L is selected from the group consisting of those groups defined in (a) or (c), above, an aromatic, alicyclic, heterocyclic, and a polycyclic ring moiety; or
(e) a —CH(D-L)$_2$ or a —C(D-L)$_3$ group where D is selected from the group —CO—, —$CO_2$—, —OCO—, —CO—NH—, —O—CO—NH—, —O—, and —S— and L is selected from the group consisting of those groups defined in (a) or (c), above, an aromatic, alicyclic, heterocyclic, and a polycyclic ring moiety and wherein two $A_1$ groups or an $A_1$ and an $A_2$ group are covalently linked with one another to form a cyclic moiety.

2. The compound of claim 1 wherein $A_1$ and $A_2$, independently of other $A_1$ and $A_2$ groups, are selected from the group consisting of a straight-chain or branched alkyl, alkenyl, or alkynyl group having from 2 to about 22 carbon atoms wherein one or more non-neighboring —$CH_2$— groups can be replaced with an O or S atom.

3. The compound of claim 2 wherein $A_1$ and $A_2$, independently of other $A_1$ and $A_2$ groups, are selected from the group consisting of a straight-chain or branched alkyl groups.

4. The compound of claim 3 wherein $A_1$ and $A_2$, independently of other $A_1$ and $A_2$ groups, are selected from the group consisting of straight-chain alkyl groups.

5. The compound of claim 1 wherein r is 0.

6. The compound of claim 1 wherein $A_1$ and $A_2$, independently of other $A_1$ and $A_2$ groups, are selected from the group consisting of a straight-chain or branched alkyl groups.

7. The compound of claim 1 wherein $A_1$ and $A_2$, independently of other $A_1$ and $A_2$ groups, are selected from the group consisting of straight-chain alkyl groups.

8. The compound of claim 1 wherein $n_i$ is 2 or 3.

9. The compound of claim 1 wherein $R_A$ and $R_B$, are selected from the group consisting of H, or an alkyl group having from 1 to 6 carbon atoms.

10. The compound of claim 1 wherein $n_i$ are integers from 2–6.

11. The compound of claim 1 wherein $n_i$ are 2, 3 or 4.

12. The compound of claim 1 wherein $A_1$ and $A_2$ are selected from the group consisting of a straight-chain or branched alkyl group having from 14 to about 22 carbon atoms.

13. The compound of claim 1 wherein $A_1$ and $A_2$ are straight-chain alkyl groups or substituted alkyl groups wherein the substituent can be an aromatic, alicyclic heterocyclic or polycyclic ring and wherein one or more of the non-neighboring —$CH_2$— groups of said alkyl, alkenyl or alkynyl group can be substituted with an O or S atom.

14. The compound of claim 1 wherein $A_1$ and $A_2$ are straight-chain alkyl groups or substituted alkyl groups wherein the substituent can be an OH group and $NH_2$ group or an amine group.

15. The compound of claim 1 wherein at least one of the $A_1$ and $A_2$ groups is a straight-chain alkyl group having 2 carbon atoms.

16. The compound of claim 1 wherein at least one of the $A_1$ and $A_2$ groups is a straight-chain alkyl group having from 2 to about 22 carbon atoms.

17. The compound of claim 1 wherein one of the $A_1$ and $A_2$ groups is a straight-chain alkyl group having 2 carbon atoms and another of the $A_1$ and $A_2$ groups is a straight-chain alkyl group having 2 to about 22 carbon atoms.

18. The compound of claim 1 wherein at least one of the $A_1$ and $A_2$ groups is a straight-chain alkyl group having 2 to 5 carbon atoms.

19. The compound of claim 1 wherein at least one of the $A_1$ and $A_2$ groups is a straight-chain alkyl group having 2 to 10 carbon atoms.

20. A compound having the formula:

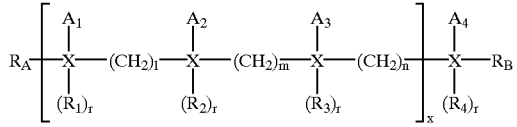

and salts thereof
wherein X is N;
x is an integer from 1 to 10;
l, m, and n, independently of one another, are integers ranging in volume from 1 to about 6;
r is 0 or 1 with N positively charged when r is 1;
$R_A$ and $R_B$, independently of one another, are selected from the group consisting of H, an alkyl, hydroxyalkyl, and a thiol-substituted alkyl group having from 1 to 6 carbon atoms;

$R_1$–$R_4$, independently of one another, are selected from the group of alkyl groups having from 1 to about 6 carbon atoms;

$A_1$–$A_3$, independently of other $A_1$–$A_3$ groups and $A_4$ are selected from the group consisting of
(a) a straight-chain or branched alkyl, alkenyl, or alkynyl group having from 2 to about 22 carbon atoms wherein one or more non-neighboring —$CH_2$— groups can be replaced with an O or S atom;
(b) a straight-chain or branched alkyl group substituted with one or two OH, SH, $NH_2$ or amine groups within about 3 carbon atoms of the bond between $A_1$ or $A_2$ and N;
(c) a substituted straight-chain or branched alkyl, alkenyl or alkynyl group having from 2 to about 22 carbon atoms wherein the substituent is an aromatic, alicyclic heterocyclic or polycyclic ring and wherein one or more of the non-neighboring —$CH_2$— groups of said alkyl, alkenyl or alkynyl group can be substituted with an O or S atom;
(d) a-B-L group where B is selected from the group consisting of —CO—, —$CO_2$—, —OCO—, —CO—NH—, —O—CO—NH—, —O—$CH_2$—, —S—$CH_2$—, —$CH_2$—S—, and —$CH_2$— and L is selected from the group consisting of those groups defined in (a) or (c), above, an aromatic, alicyclic, heterocyclic, polycyclic ring moiety; and
(e) a —CH(D-L)$_2$ or a —C(D-L)$_3$ group where D is selected from the group consisting of —CO—, —$CO_2$—, —OCO—, —CO—NH—, —O—CO—NH—, —O—, and —S— and L is selected from the group consisting of those groups defined in (a) or (c), above, an aromatic, alicyclic, heterocyclic, and a polycyclic ring moiety and
wherein at least two of the $A_1$–$A_4$ groups are covalently linked to form a cyclic moiety.

21. The compound of claim 20 wherein x is 2.
22. The compound of claim 20 wherein r is 0.
23. The compound of claim 20 wherein r is 1.
24. The compound of claim 20 wherein m is 1.
25. The compound of claim 20 wherein x is 1.
26. The compound of claim 25 wherein $A_2$ and $A_3$ groups are straight-chain alkyl group having 2 carbon atoms which are covalently linked with one another to form a cyclic moiety.
27. The compound of claim 26 wherein $A_1$ and $A_4$ groups are straight-chain alkyl group having 2 to about 22 carbon atoms.
28. The compound of claim 27 wherein l and n are 3 and m is 2.
29. The compound of claim 28 wherein $R_A$ and $R_B$ are hydrogens.
30. The compound of claim 29 wherein r is 0.
31. The compound of claim 1 wherein r is 1.
32. The compound of claim 1 wherein $A_1$ and $A_2$ alkyl groups are substituted with one or two $NH_2$ groups.
33. The compound of claim 1 wherein $A_1$ and $A_2$ alkyl groups are substituted with one or two OH groups.
34. The compound of claim 1 wherein $A_1$ and $A_2$ are selected from the group consisting of a substituted straight-chain or branched alkyl group wherein the substituents on said alkyl group are alicyclic rings or aromatic rings.
35. The compound of claim 1 wherein $A_1$ and $A_2$ are selected from the group consisting of a -B-L group where B is selected from the group consisting of —CO—, —$CO_2$—, —OCO—, —CO—NH—, —O—CO—NH—, —$OCH_2$—, —S—$CH_2$—, —$CH_2$—S—, and —$CH_2$— and L is selected from the group consisting of those groups defined in (a) or (c), an aromatic, alicyclic, heterocyclic, and a polycyclic ring moiety.

36. The compound of claim 35 wherein B is —O—$CH_2$—.
37. The compound of claim 35 wherein B is —CO—N— or —O—CO—N—.
38. The compound of claim 35 wherein L is a straight-chain or branched alkyl, alkenyl, or alkynyl group having from 2 to about 22 carbon atoms wherein one or more non-neighboring —$CH_2$— groups can be replaced with an O or S atom.
39. The compound of claim 1 wherein $A_1$ and $A_2$ are selected from the group consisting of a —CH(D-L)$_2$ or a —C(D-L)$_3$ group where D is selected from the group consisting of —CO—, —$CO_2$—, —OCO—, —CO—NH—, —O—, and —S— and L is selected from the group consisting of those defined in (a) or (c) an aromatic, alicyclic, heterocyclic and polycyclic ring moiety.
40. The compound of claim 1 wherein L is a straight-chain or branched alkyl, alkenyl, or alkynyl group having from 2 to about 22 carbon atoms wherein one or more non-neighboring —$CH_2$— groups can be replaced with an O or S atom.
41. A lipid aggregate which comprises one or more compounds of claim 1.
42. A lipid aggregate of claim 41 further comprising one or more phospholipids.
43. A lipid aggregate which comprises one or more compounds of claim 20.
44. A composition for transfecting a cell which comprises a compound of claim 1 and a nucleic acid.
45. A composition for transfecting a cell of claim 44 further comprising one or more amphipathic lipids.
46. A composition for transfecting a cell of claim 44 further comprising a phospholipid.
47. A composition for transfecting a cell which comprises a lipid aggregate of claim 41 and a nucleic acid.
48. A composition for transfecting a cell which comprises a compound of claim 20 and a nucleic acid.
49. A kit for preparing a lipid aggregate comprising one or more compounds of claim 1.
50. The kit of claim 49 further comprising one or more phospholipids.
51. A kit for preparing a lipid aggregate comprising one or more compounds of claim 20.
52. A method for transfecting a cell comprising the step of contacting said cell with a lipid aggregate comprising a nucleic acid and a compound of claim 1.
53. A method for transfecting a cell comprising the step of contacting said cell with the composition of claim 44.
54. A method for transfecting a cell comprising the step of contacting said cell with the composition of claim 20.
55. A method for delivery of a macromolecule to a cell comprising the step of contacting said cell with a composition which comprises a compound of claim 1 and said macromolecule.
56. The method of claim 55 wherein the macromolecule is an anionic molecule.
57. A method for delivery of a macromolecule to a cell comprising the step of contacting said cell with a composition which comprises a compound of claim 20 and said macromolecule.

* * * * *

UNITED STATES PATENT AND TRADEMARK OFFICE
CERTIFICATE OF CORRECTION

PATENT NO. : 6,110,916
DATED : August 29, 2000
INVENTOR(S) : Haces et al.

It is certified that error appears in the above-identified patent and that said Letters Patent is hereby corrected as shown below:

Column 1,
Line 33, after "Lipid aggregates containing DNA are known to be effective agents for efficient transfection of target cells.", delete "aggregates containing DNA are known to be effective agents for efficient transfection of target cells."

Column 3,
Line 38, delete "The highly packed and spatially correct positioning of positive charges matching negative charges on DNA" and insert -- The highly packed and spatially correct positioning of positive charges, matching negative charges on DNA, of --.

Column 10,
Line 57, under section heading DEFINITIONS, delete "amphiphatic" and insert -- amphipathic --.

Column 19,
Line 53, within Scheme 4, delete "Na$_2$Sl" and insert -- Na$_2$S / --.

Column 21,
Line 17, delete "R$_A$ and R$_B$, independently or one another," and insert -- R$_A$ and R$_B$, independently of one another --.

Column 22,
Line 62, delete "l, m, and n, independently of one another, are integers ranging in volume from 1 to about 6;" and insert -- l, m, and n, independently of one another, are integers ranging in value from 1 to about 6; --.

Signed and Sealed this

Thirtieth Day of April, 2002

*Attest:*

*Attesting Officer*

JAMES E. ROGAN
*Director of the United States Patent and Trademark Office*